United States Patent [19]
Jolly et al.

[11] Patent Number: 5,741,289
[45] Date of Patent: Apr. 21, 1998

[54] CLEANABLE GUARDED SURGICAL SCALPEL WITH SCALPEL BLADE REMOVER

[75] Inventors: Neil Jolly, Brighton, Mass.; Craig D. Newman, New York, N.Y.; Robert W. Pierce, Wrentham, Mass.

[73] Assignee: Becton, Dickinson and Company, Franklin Lakes, N.J.

[21] Appl. No.: 756,300

[22] Filed: Nov. 25, 1996

Related U.S. Application Data

[63] Continuation of Ser. No. 547,699, Oct. 19, 1995.

[51] Int. Cl.$^6$ .................................................. A61B 17/14
[52] U.S. Cl. ............................................ 606/181; 606/172
[58] Field of Search .................................. 606/167, 172, 606/181, 182

[56] References Cited

U.S. PATENT DOCUMENTS 5,330,494  7/1994  van der Westheinzen et al. .... 606/167

*Primary Examiner*—Michael Buiz
*Assistant Examiner*—Kevin Truong
*Attorney, Agent, or Firm*—Arthur D. Dawson; Eric M. Lee; John L. Voellmicke

[57] ABSTRACT

This invention relates to an improved guarded surgical scalpel having a movable guard that can be retracted to expose the blade and that can be extended to cover the sharp cutting edge of the blade. The guard is also mounted for rotatable movement with respect to the handle. A blade carrier is mounted to the guard to allow relative longitudinal movement between the guard and the blade carrier. The blade carrier is also removably mounted to the handle. This mounting arrangement for the handle, guard and blade carrier allows the guard and blade carrier to be rotated away from the handle so the surfaces of the handle, guard and blade carrier can be exposed. This facilitates cleaning of the guarded surgical scalpel after use.

13 Claims, 5 Drawing Sheets

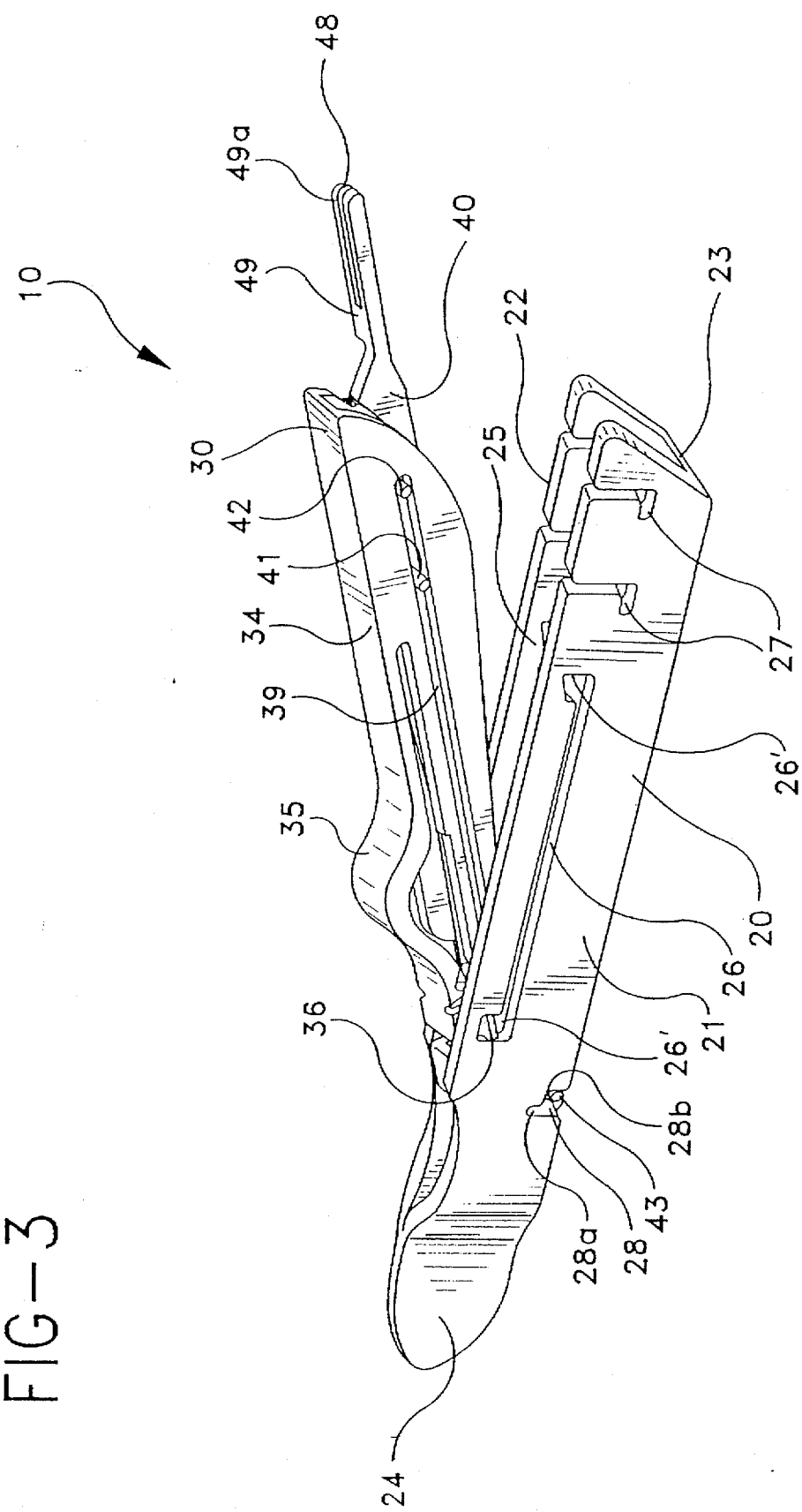

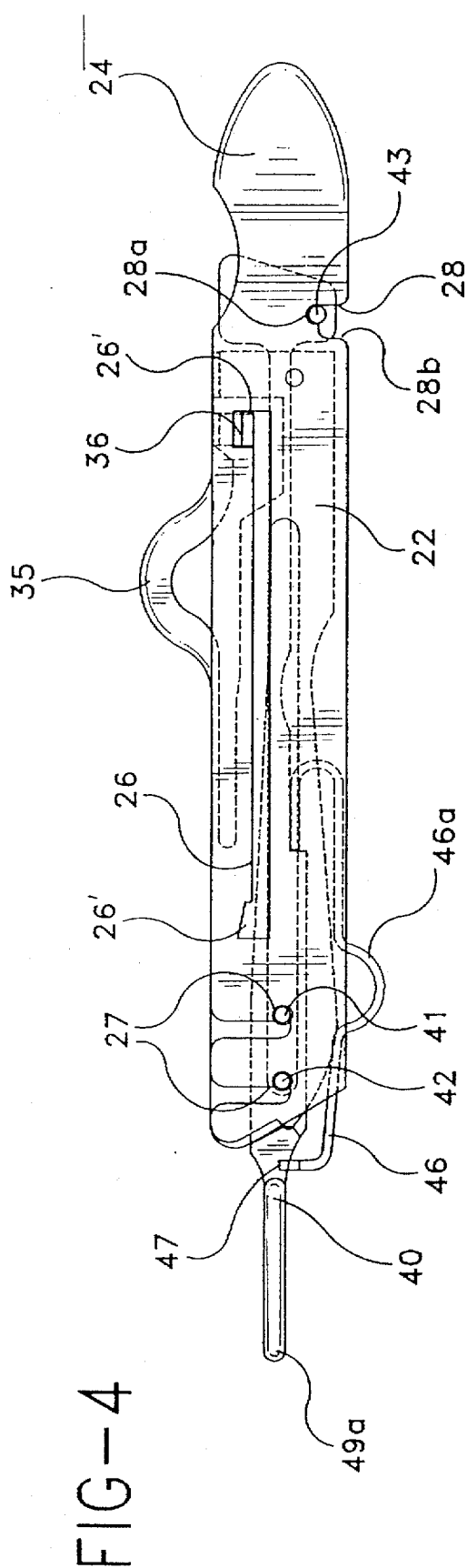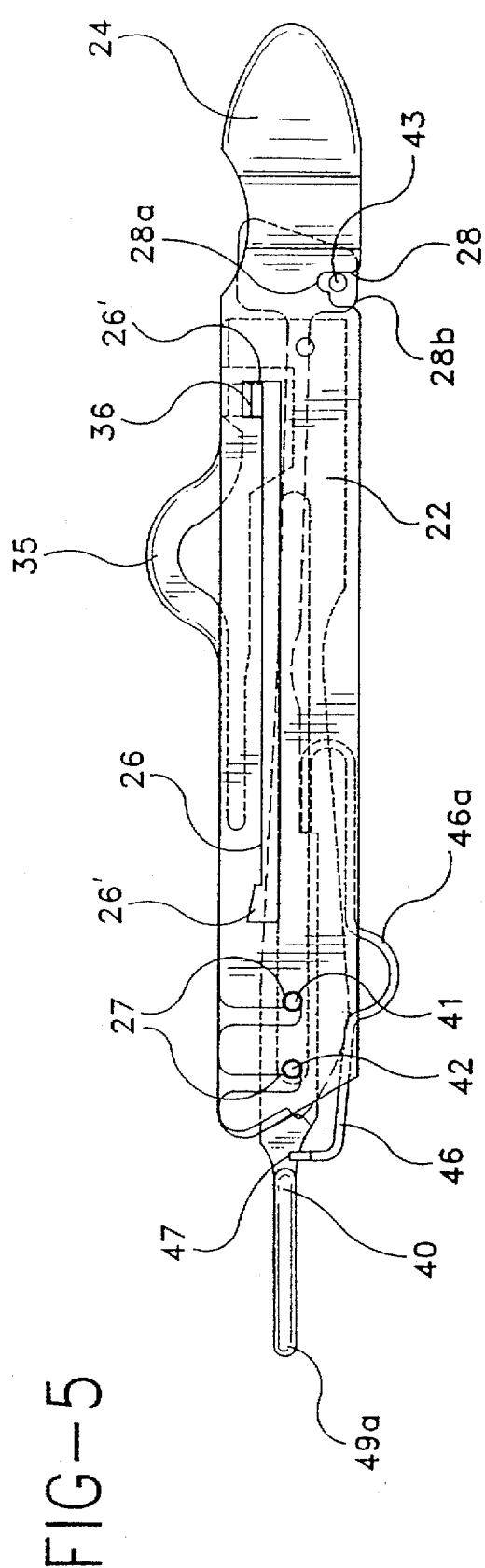

CLEANABLE GUARDED SURGICAL SCALPEL WITH SCALPEL BLADE REMOVER

This is a continuation of application Ser. No. 08/547,699, filed Oct. 19, 1995.

BACKGROUND OF THE INVENTION

The present invention relates to a surgical scalpel and, in particular, to a surgical scalpel having a retractable blade guard that can be used to cover the blade to protect healthcare professionals from being inadvertently nicked or cut when the surgical scalpel is handled, especially during a surgical procedure in an operating room. In addition, this invention relates to a unique mechanism for removing the blade from the handle for disposal either during or at the end of the surgical procedure. Moreover, this invention combines all of the above features in a surgical scalpel that may be partially disassembled to facilitate cleaning and sterilization of the surgical scalpel. Finally, this invention includes a locking mechanism that prevents inadvertent partial disassembly of the surgical scalpel prior to the need to clean and sterilize the device.

Scalpels are regularly used by surgeons and other healthcare professionals for making incisions in a patient during an operating procedure. Typically, a nurse hands the scalpel to the surgeon in a predetermined orientation so that the surgeon can grip the scalpel's handle without taking his or her eyes away from the patient. If the nurse accidentally touches the scalpel when it is on the table, does not pay close attention when picking up the scalpel or if the predetermined orientation is not closely followed when the scalpel is transferred to the surgeon, the nurse's or surgeon's hand may be cut or nicked by the blade of the scalpel. The same hazard of being cut or nicked by the blade may be encountered when the surgeon transfers the scalpel back to the nurse.

These nicks or cuts are uncomfortable and distracting. In addition, they may result in blood or body fluid exposure between the patient and the surgeon or other healthcare professionals in the operating room or elsewhere in the hospital. This may lead to the spread of infectious diseases between the patient and the healthcare professional. Concern over this situation has become especially acute because of such diseases as acquired immune deficiency syndrome, i.e. AIDS, and hepatitis.

While surgical gloves aid in reducing the chances of being cut during a surgical procedure, these gloves are not foolproof. And even when two sets of gloves are utilized, full protection is not afforded to the healthcare provider because the scalpel blade can still cut through both sets of gloves. Also, utilizing two sets of gloves reduces finger dexterity by the surgeon and thus is distracting to the surgeon and can interfere with the intended surgical procedure.

In view of the need for a surgical scalpel that can prevent or at least minimize the chances of accidental nicks or cuts during handling, numerous guarded surgical scalpels have been recently designed. Unfortunately, these designs are deficient because they are cumbersome, difficult to use, may cause unwanted shielding or exposure of the scalpel blade prior to the need for such shielding or exposure or may require considerable attention by the user to shield or expose the blade. In addition, these prior designs are deficient because they do not provide a safe and effective way for the blade to be removed from the handle either during or after the surgical procedure. Typically the blade tang has to be grasped by the user's hand or by a clamp and pulled from the handle. This procedure is not desirable because it exposes the person attempting to remove the blade to the risk of being cut if the user's hand is used to grasp the blade tang. And even if a clamp is used, this procedure is cumbersome at best.

Another shortcoming of these other guarded surgical scalpel designs is that they are difficult to clean and sterilize. These designs typically include some shielding mechanism to extend and retract either (i) a guard over or from the blade or (ii) the blade out of or into the handle to prevent contact between healthcare professional and the sharp cutting edge of the blade. Usually a significant portion of the shielding mechanism resides inside the handle. This makes cleaning the guarded surgical scalpel difficult because in a surgical procedure blood and other body fluids will contaminate a significant portion of the inside and outside of the scalpel. Indeed it would not be unusual for the entire scalpel to be immersed in such body fluids at some point in the surgical procedure. Unfortunately, after the surgical procedure is completed, these scalpels typically are not immediately cleaned. In fact, it may be quite some time before the scalpels are cleaned and sterilized for reuse. During this time, the body fluids contaminating the used scalpel will dry and harden to the point that they tenaciously adhere to the scalpel. Thus, it is not a simple matter to immerse the used scalpel in a cleaning solution to completely clean the scalpel. Instead, some surfaces have to be scrubbed with some abrasive material in order to be cleaned. This may be difficult or even impossible for portions of the scalpel, especially those portions of the scalpel housed in the interior of the scalpel such as the shielding mechanism.

SUMMARY OF THE INVENTION

It is therefore an object of this invention to provide a guarded surgical scalpel that prevents or at least minimizes the chance that the healthcare professional will be nicked or cut when the guarded surgical scalpel is handled.

It is another object of this invention to provide a guarded surgical scalpel that is easy to use and that can be operated by one hand of the user.

It is yet another object of this invention to provide a guarded surgical scalpel that will not allow the blade to be shielded or exposed prior to the need to do so.

It is still another object of this invention to provide a guarded surgical scalpel that can be used without the need for the user to observe the movement of the guard or to place undue attention to its operation.

It is still a further object of this invention to provide a guarded surgical scalpel that allows for the safe and effective removal of the blade from the handle after use.

It is yet a further object of this invention to provide a guarded surgical scalpel that is easily cleanable after use.

This invention comprises a guarded surgical scalpel including a handle, a blade carrier operatively connected to the handle, and a guard telescopically mounted within the handle and about the blade carrier for sliding movement between a retracted position and an extended position. A unique detent mechanism is provided between the guard and the handle for defining the extended position and the retracted position of the guard on the handle. The detent mechanism comprises a slot with upturned ends formed in at least one sidewall of the handle and a movable top wall formed in the guard which has a radially extending flange formed therein. This flange engages and rides in the slot formed in the sidewall of the handle. The top wall of the guard, and thus the flange, is biased upwardly so that the flange is captured in the upturned ends of the slot when the guard is in the fully extended and fully retracted position. This arrangement of the flange and the upturned ends of the slot prevent longitudinal movement of the guard by the application of only a longitudinal force to the guard by the user when the guard is in the fully extended and fully retracted position. The user, however, can move the guard by simply depressing the top wall of the guard to move the flange out of engagement with the upturned ends of the slot.

The blade carrier typically has a blade removably connected thereto. The distal end of one sidewall of the guard may be formed with a notch that complements a notch formed in the proximal end of the tang of the blade. By merely aligning the notch on the sidewall of the guard with the notch on the blade tang, forward movement of the guard will force the blade off of the blade carrier. Alignment between the notch on the sidewall of the guard and the notch on the blade tang is provided by a movable lifter wedge on the blade carrier. This lifter wedge can be urged between the blade tang and the blade carrier to lift the blade tang away from the blade carrier.

The blade carrier is removably connected to the handle and is oriented therein to allow sliding movement of the guard past the blade carrier. Although the blade carrier is removably connected to the handle, the guard remains connected to the handle by virtue of the flange of the guard being retained in the handle slot. This particular arrangement of the handle, blade carrier and guard allows the blade carrier and guard to be removed from the interior of the handle. This provides easy access to the shielding mechanism of the guarded surgical scalpel of this invention and facilitates cleaning and sterilization thereof. The guarded surgical scalpel of this invention also includes a locking mechanism that prevents inadvertent removal of the blade carrier and guard from the interior of the handle until the guarded surgical scalpel is to be cleaned and sterilized.

The blade carrier includes at least one pin located adjacent to its distal end. This distal pin is perpendicular to the longitudinal axis of the blade carrier and extends outwardly beyond both sides of the blade carrier. The pin extends into and beyond longitudinal slots formed on both sides of the guard and into the sidewalls of the handle. In order to accommodate the pin in the sidewalls of the handle, at least one L-shaped slot is formed in each sidewall adjacent to their distal ends so the pin on the blade carrier extends into the L-shaped slot. The blade carrier also includes at least one pin adjacent to the proximal end. This proximal pin is also perpendicular to the longitudinal axis of the blade carrier and extends outwardly beyond both sides of the blade carrier into the sidewalls of the handle. The guard is preferably shorter than the blade carrier and thus, does not interfere with the proximal pin. When the distal pin is located in the horizontal portion of the L-shaped slot, the proximal pin is located in a cut-out formed in the bottom of both sidewalls of the handle. With the distal pin and proximal pin in this orientation, the blade carrier is effectively engaged with and locked to the handle. After use, the proximal portion of the blade carrier can be depressed to disengage the proximal pin on the blade carrier from the cut-out formed in the bottom of both sidewalls of the handle. This disengages and unlocks the blade carrier to allow the distal pin to become aligned with the vertical portion of the L-shaped slot. Movement of the blade carrier upwardly allows the blade carrier to completely disengage from the handle. Since the guard is connected to the blade carrier via the distal pin, the guard also moves away from the handle so all portions of the guarded surgical scalpel are accessible for cleaning and sterilization.

DESCRIPTION OF THE DRAWINGS

The above and other objects and advantages of this invention will be apparent upon consideration of the following drawings and detailed description. The preferred embodiments of the present invention are illustrated in the appended drawings in which like reference numerals refer to like elements and in which:

FIG. 3 is a perspective view of the guarded surgical scalpel of the present invention with the blade carrier and guard rotated away from the handle;

FIG. 4 is a side elevation view of the guarded surgical scalpel of the present invention with the guard in a retracted position and the blade carrier locked to the handle;

FIG. 5 is a side elevation view of the guarded surgical scalpel of the present invention with the guard in a retracted position and where the proximal portion of the blade carrier has been depressed to unlock the blade carrier from the handle;

DETAILED DESCRIPTION OF THE INVENTION

Figure 1:
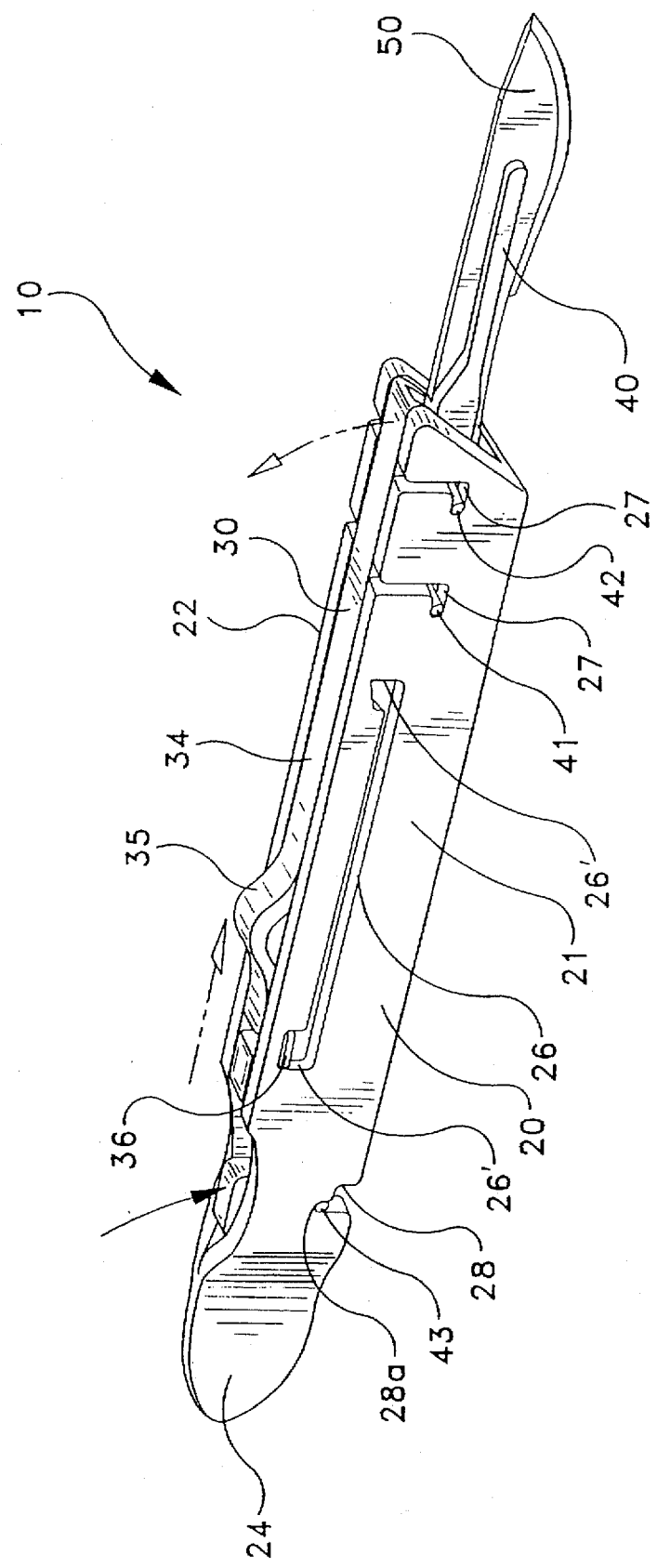
FIG. 1 is a perspective view of the guarded surgical scalpel of the present invention with the guard in a retracted position to expose the blade.
Figure 2:
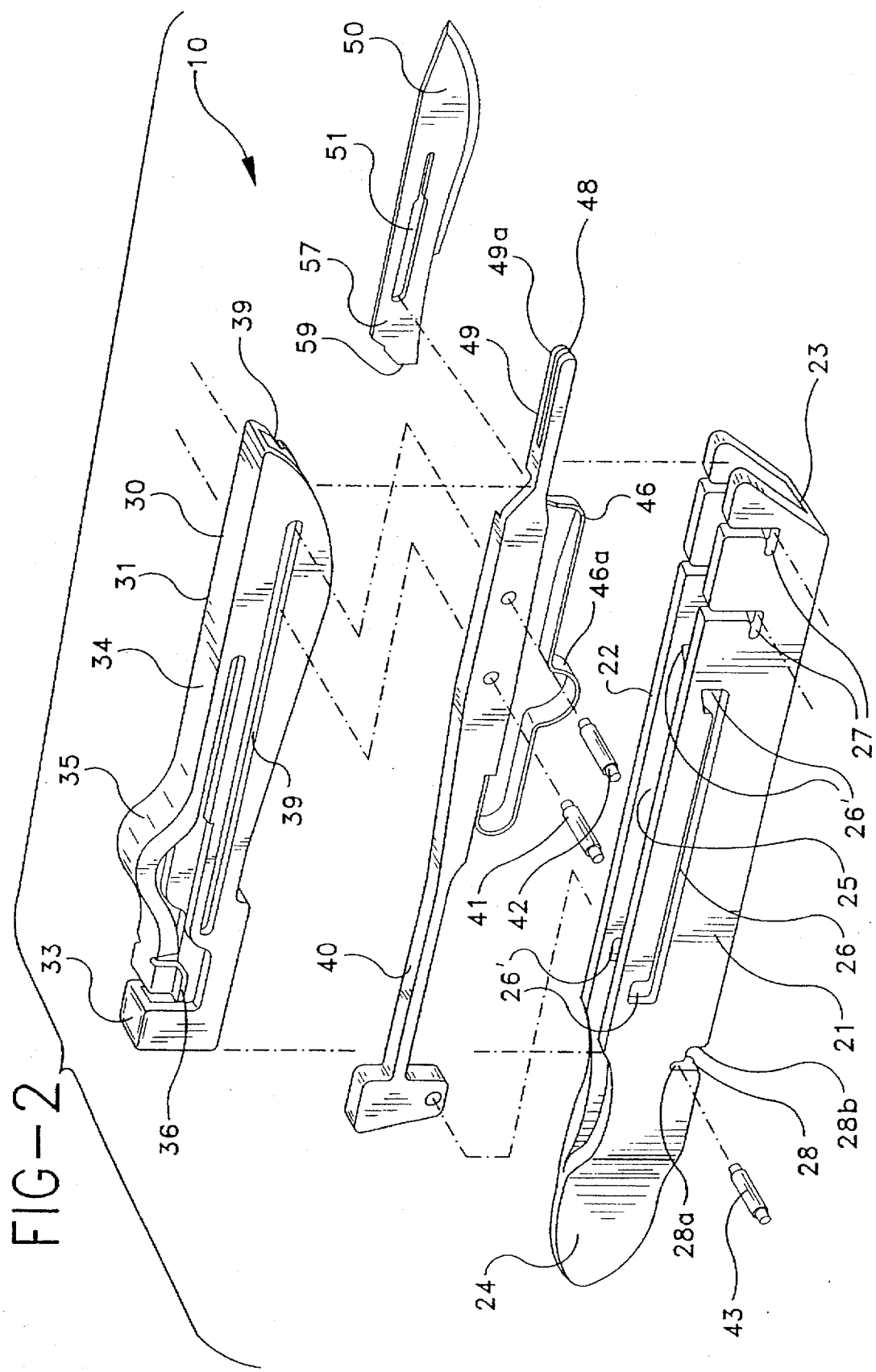
FIG. 2 is an exploded perspective view of the guarded surgical scalpel of the present invention.

The guarded surgical scalpel 10 of the present invention includes a handle 20 having a guard 30 slidably and rotatably mounted to handle 20 and a blade carrier 40 that is removably locked to handle 20 and slidably mounted to guard 30. Although the following description of handle 20, guard 30 and blade carrier 40 refers to only one side of these elements, it is to be understood that each side of each element is a mirror image of the other side of that element, except where explicitly stated otherwise. In addition, the references to up and down hereinafter refer to the top and bottom respectively of the sheet of drawings on which the guarded surgical scalpel of this invention is illustrated when the sheet is in the landscape position.

Handle 20 has two parallel sidewalls 21, 22, a bottom wall 23 and a closed proximal end 24. This configuration for handle 20 defines a cavity 25 therein. Proximal end 24 of handle 20 is tapered to a thin portion to provide a blunt dissection tool that can be used during the operating procedure. Sidewalls 21 and 22 of handle 20 preferably each define a longitudinal slot 26 therein that are substantially aligned. Each longitudinal slot 26 is generally parallel to the longitudinal axis of handle 20. In addition, the ends of each longitudinal slot 26 has upturned portions 26' extending away from the main portion of longitudinal slot 26. Sidewalls 21 and 22 also each define at least one and preferably two L-shaped slots 27 adjacent to the distal end of handle 20 and a cut-out 28 adjacent to the proximal end of handle 20.

In order to have a comfortable and functional product, handle 20 preferably has an overall length of about 4.180 inches, an overall width of about 0.310 inches and an overall height of about 0.520 inches. Preferably longitudinal slots 26 each have an overall length of about 1.875 inches.

Blade carrier 40 includes a plurality of transverse pins 41, 42 and 43 that are perpendicular to the longitudinal axis of blade carrier 40 and extend beyond either side of blade carrier 40 to extend the width of handle 20. Pin 43 is located adjacent to the proximal end of blade carrier 40, while pins 41 and 42 are located adjacent to the distal end of blade carrier 40. Pins 41, 42 and 43 can be bonded to blade carrier 40 by any conventional means such as orbital riveting, chemical adhesive, ultrasonic bonding or welding or brazing. Alternatively, pins 41, 42 and 43 can be unitarily molded with blade carrier 40. Blade carrier 40 fits within cavity 25 of handle 20 such that pins 41 and 42 extend into L-shaped slots 27 and pin 43 extends into cut-out 28. Cut-out 28 has a two step configuration. When pin 43 is in step 28a, pins 41 and 42 extend into the horizontal portions of L-shaped slots 27 to effectively lock blade carrier 40 to handle 20. Thus, a longitudinally directed force on the distal end of blade carrier 40 will not move blade carrier 40 because pin 43 is effectively locked in step 28a. Similarly, an upwardly or downwardly directed force on the distal end of blade carrier 40 will not move blade carrier 40 because pins 41 and 42 are effectively locked in the horizontal portion of L-shaped slots 27. As discussed more fully below, blade carrier 40 may be disengaged from handle 20 to facilitate cleaning and sterilization thereof.

When blade carrier 40 is locked to handle 20, blade carrier 40 extends forwardly of handle 20 in a cleat 49 and has a laterally-extending longitudinal rib 49a provided with an external groove 48. Blade 50 has a longitudinal slot 51 which cooperates with groove 48 and rib 49a to mount blade 50 on blade carrier 40, thereby mounting blade 50 on handle 20. Blade 50 is relatively thin and has a very sharp edge and is "snapped" over rib 49a on blade carrier 40. Blade carrier 40 may include a notch 44 formed therein that mates with another notch 59 formed in the blade tang 57. This configuration may be used, if desired, to ensure that only the appropriate blades are used with guarded surgical scalpel 10.

A cantilever spring arm 46 may also be formed in blade carrier 40. The distal end of cantilever spring arm 46 includes a wedge shaped portion 47 that aligns with the interface between blade cleat 49 and blade 50. Spring arm 46 and wedge 47 are arranged on blade carrier 40 so that the tip of wedge 47 extends to cleat 49 in the unbiased condition. In this way, the tip of wedge 47 is already in the interface between cleat 49 and blade tang 57. By moving cantilever spring arm 46 toward this interface by pushing button 46a, wedge 47 causes blade tang 57 to move away from cleat 49 to facilitate removal of blade 50 from blade carrier 40. Preferably, cantilever spring arm 46 is about 1 inch long and about 0.125 inches wide. It is connected to blade carrier 40 via a flexural hinge to facilitate movement of wedge 47 toward the interface between cleat 49 and blade tang 57.

Wedge 47 and blade carrier 40 are configured to provide a detent mechanism that holds wedge 47 in the interface between blade cleat 49 and blade tang 57. In this way, the healthcare professional need not constantly squeeze spring arm 46 to raise blade tang 57. Instead, the detent mechanism holds wedge 47 in the interface between blade cleat 49 and blade tang 57. Once blade 50 has been removed from blade carrier 40, the detent mechanism allows spring arm 46 to return to its unbiased position. Alternatively, guard 30 could be formed with a shoulder formed on an internal wall thereof. This shoulder holds spring arm 46 so wedge 47 remains at the interface between blade cleat 49 and blade tang 57. Once guard 30 is advanced to remove blade 50 from blade cleat 49, as discussed in more detail below, the shoulder on guard 30 is located beyond spring arm 46 to allow spring arm 46 to return to its unbiased position.

Guard 30 preferably has two parallel sidewalls 31, 32 which are connected by a proximal top wall 33 and a distal top wall 34. Preferably the distal portion of sidewalls 31, 32 have a shape similar to that of a standard surgical scalpel blade. Using this shape for the distal portion of sidewalls 31, 32 helps the user of guarded surgical scalpel 10 intuitively to understand how to hold and use guarded surgical scalpel 10. Sidewalls 31 and 32 each define a longitudinal slot 39 which extends along substantially the entire length of sidewalls 31 and 32.

Distal top wall 34 is connected to sidewalls 31 and 32 only along a distal portion of distal top wall 34. This allows the proximal portion of distal top wall 34 to be flexed downwardly in a cantilevered fashion. The proximal portion of distal top wall 34 carries a bump 35 formed therein to facilitate downward flexing of the proximal portion of distal top wall 34. Alternatively, the proximal portion of distal top wall 34 can be formed with a detent button therein to facilitate downward flexing of the proximal portion of distal top wall 34. Detent flanges 36 are located adjacent to the proximal end of distal top wall 34 on both sides thereof and may be bonded thereto by press fit, welding or chemical adhesive. Alternatively and preferably, flanges 36 are integrally formed along with distal top wall 34. By using flanges 36 instead of a separate element, i.e. a pin, the manufacturing of guarded surgical scalpel 10 is facilitated.

Guard 30 is preferably mounted in cavity 25 of handle 20 for telescopic movement therein and should be dimensioned to allow a tight yet movable fit therein. In order to allow such movement by guard 30, blade carrier 40 is centrally located within guard 30 with pins 41 and 42 extending through slots 39 of guard 30 into L-shaped slots 27. By placing guard 30 within cavity 25, flanges 36 extend into and ride in longitudinal slots 26 formed in sidewalls 21, 22 of handle 20. Flanges 36 are biased into the upturned portions provided at the ends of the longitudinal slots 26 when guard 30 is in the fully extended or the fully retracted position. The length of longitudinal slots 26 formed in sidewalls 21, 22 of handle 20 is equal to the amount of travel of guard 30 from its fully retracted position to its fully extended position.

When flanges 36 are located in the upturned portions at the ends of longitudinal slots 26 formed in sidewalls 21, 22 of handle 20, guard 30 is temporarily locked in the extended or retracted position. If the user were to inadvertently apply a longitudinal force to guard 30 when guard 30 was in one of these positions, guard 30 would not move. In order to move guard 30, a downward force must be applied to distal top wall 34 via bump 35 to move flanges 36 out of engagement with the upturned portions at the ends of longitudinal slots 26. Thus, the chance that the user would inadvertently shield or expose blade 50 prior to the need to do so is minimized. In addition, because of the upward bias of distal top wall 34, and thus flanges 36, the user will automatically know when guard 30 has been moved completely to the fully extended or fully retracted position by an audible "click" when flanges 36 engage one of the upturned portions at the ends of longitudinal slots 26.

In order to allow the user to flex distal top wall 34 downwardly with a comfortable force, distal top wall 34 should be connected to sidewalls 31, 32 only along about 1.1 inches of the distal-most portion of distal top wall 34 when guard 30 is formed from stainless steel. If a softer material, such as plastic, is used this distance could be longer. This arrangement results in upper slots being formed in distal top wall 34. These upper slots should have a height of about 0.065 inches. These dimensions allow sufficient downward movement of flanges 36 so they can be moved out of engagement from the upturned portions of longitudinal slots 26.

Sidewall 32, which is adjacent to blade 50, may have a notch 39 formed at its distal end that mates with notch 59 formed on blade tang 57. This configuration allows blade 50 to be easily removed from blade carrier 40 without the need for the healthcare professional to grasp blade 50 with this hand. By slightly lifting blade tang 57 with cantilever spring arm 46, notch 39 of guard 30 can engage notch 59. Once these notches are engaged, guard 30 can be advanced distally to force blade 50 from blade carrier 40. If desired, sidewall 31 could also have a notch that matches notch 35.

As is readily apparent from the above description, guarded surgical scalpel 10 is simple to use. With blade carrier 40 locked to handle 20, guard 30 may be fully retracted to expose the distal end of blade carrier 40. Blade 50 may then be "snapped" over rib 49a. A healthcare professional may then depress bump 35 to move guard 30 to its fully extended position. Guarded surgical scalpel 10 may then be safely handled by other healthcare professionals. When guarded surgical scalpel 10 is ready for use in a surgical procedure, the healthcare professional may depress bump 35 to move guard 30 to its fully retracted position to expose the sharp cutting edge of blade 50. After use, the healthcare professional may depress bump 35 to move guard 30 to its fully extended position to once again allow guarded surgical scalpel 10 to be safely handled.

When guarded surgical scalpel 10 is ready for cleaning and sterilization, bump 35 may be depressed to allow guard 30 to be moved to its fully retracted position. Button 46a may then be depressed to lift blade tang 57 away from blade cleat 49. Bump 35 may then be depressed to move guard 30 toward its extended position to allow notch 39 to be aligned with notch 59. Further distal movement of guard 30 will then eject blade 50 from blade carrier 40.

Figure 6:
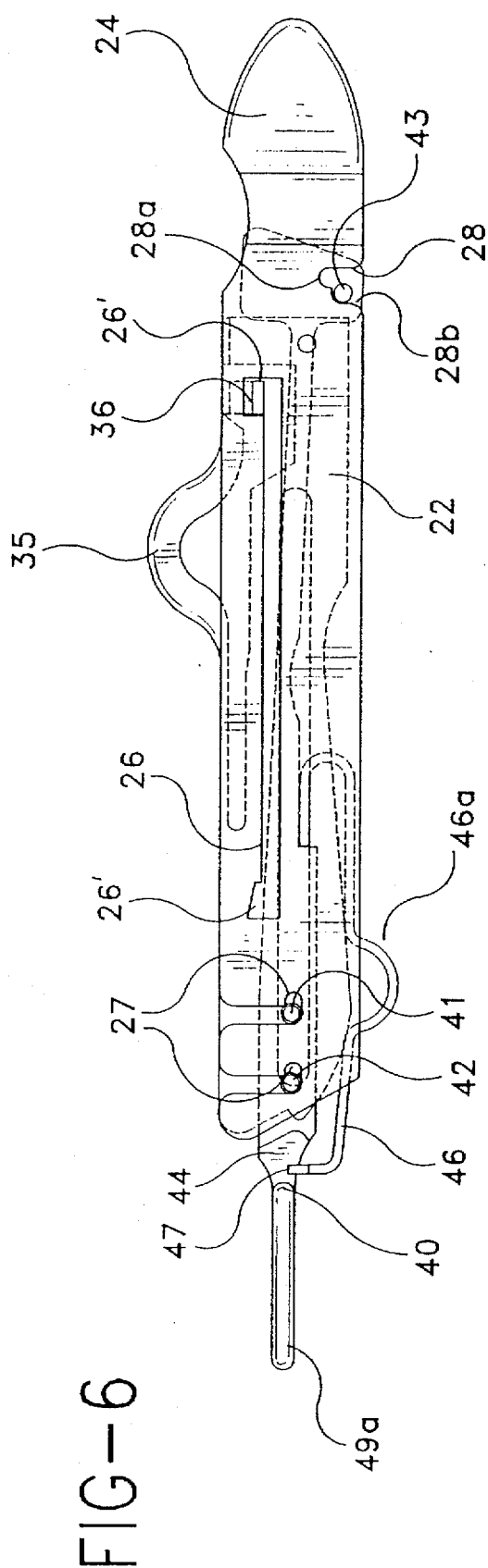
FIG. 6 is a side elevation view of the guarded surgical scalpel of the present invention with the guard in a retracted position and where the blade carrier has been moved forward to disengage the blade carrier from the handle.
Figure 7:
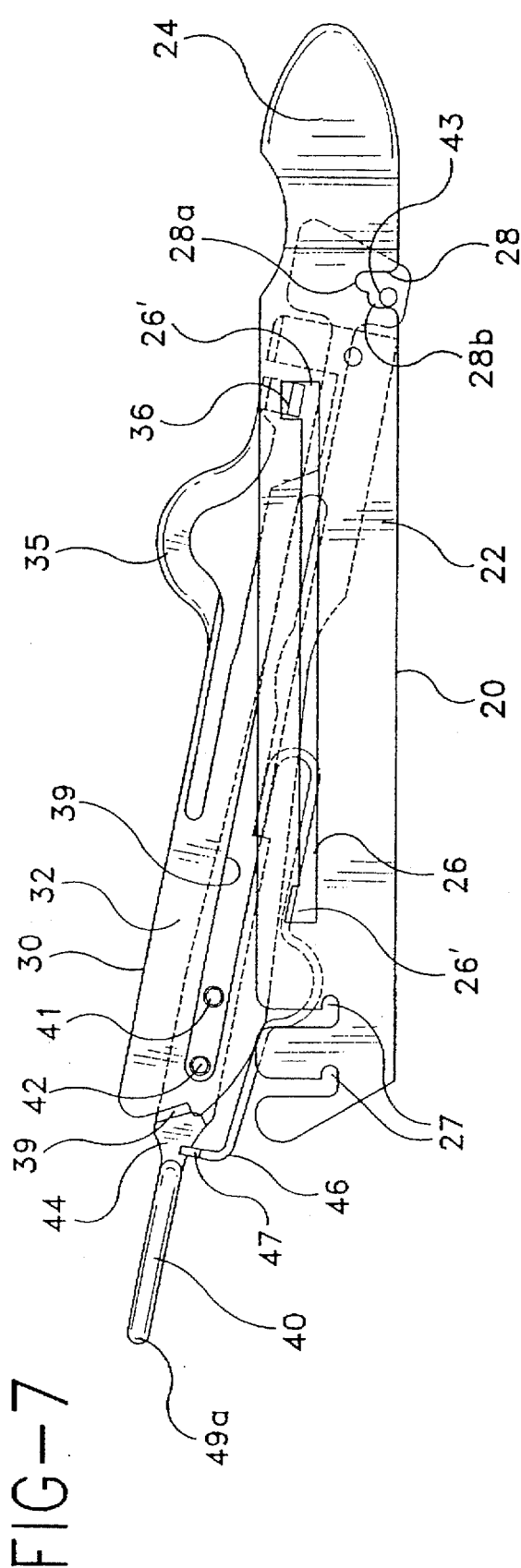
FIG. 7 is a side elevation view of the guarded surgical scalpel of the present invention with the blade carrier disengaged and rotated away from the handle and the guard rotated away from the handle.

After removal of blade 50 from blade carrier 40, guard 30 and blade carrier 40 are preferably rotated away from handle 20. This exposes virtually every surface of guarded surgical scalpel 10 for cleaning and sterilization. In order to rotate guard 30 and blade carrier 40, blade carrier 40 must be unlocked from handle 20. This is accomplished by depressing the proximal portion of blade carrier 40 to move pin 43 out of step 28a of cut-out 28. Compare FIG. 4 with FIG. 5. At that point, blade carrier 40 can be moved distally a short distance, i.e. the length of the horizontal portions of L-shaped slots 27, to bring pins 41 and 42 into alignment with the vertical portions of L-shaped slots 27. See FIG. 6. Once pins 41 and 42 are so aligned, blade carrier 40 may be rotated up and away from handle 20 with pin 43 acting as the pivot point in step 28b of cut-out 28. Guard 30 can be rotated away from handle 20 with blade carrier 40 because guard 30 pivots about flanges 36 in longitudinal slots 26. Of course, longitudinal slots 26 and flanges 36 must be dimensioned to allow such rotation. Preferably, rotation of guard 30 occurs when guard 30 has been fully retracted so flanges 36 are located in the proximal upturned portions of longitudinal slots 26. Continued upward movement of blade carrier 40 completely disengages blade carrier 40 from handle 20 and rotates guard 30 away from handle 20. See FIG. 7. The bottom of handle 20 defines open spaces to allow rotation of guard 30 and blade carrier 40 away from handle 20. At this point, guarded surgical scalpel 10 may be easily cleaned and sterilized.

Handle 20, guard 30 and blade carrier 40 are all preferably formed from 410 stainless steel. However, 303 stainless steel or 420 stainless steel could also be used. Because guard 30 slides past handle 20 and blade carrier 40, guard 30 is preferably treated with titanium nitride or chromium nitride vapor deposition. This process hardens the surface of guard 30 to prevent galling and ensures smooth operation of guarded surgical scalpel 10 over its useful life.

Thus, it is seen that a guarded surgical scalpel is provided that prevents, or at least minimizes, the chances for nicks or cuts during handling, that is easy to use and can be operated by one hand of the user, that will not allow the blade to be shielded or exposed prior to the need to do so, that can be used without the need for the user to observe the movement of the guard or to place undue attention to its operation, that provides a simple, safe and effective way to remove the blade from the handle and that is easily cleanable.

We claim:

1. A guarded surgical scalpel, comprising:
   the elongate handle;
   a guard mounted to the handle for longitudinal movement between an extended position and a retracted position and rotary movement with respect to the handle;
   a blade carrier mounted to the guard for longitudinal movement with respect to the guard and rotary movement with respect to the handle; a blade mounted on the blade carrier and
   a wedge movably mounted to the blade carrier, the wedge being movable to a position toward the blade carrier to facilitate removal of the blade from the blade carrier.

2. The guarded surgical scalpel of claim 1 wherein the handle includes two sidewalls which define a cavity therebetween and the guard and the blade carrier are located within the cavity.

3. The guarded surgical scalpel of claim 2 wherein the blade carrier is located within the guard.

4. The guarded surgical scalpel of claim 3 wherein the guard defines a flange adjacent a proximal portion of the guard and one of the two sidewalls defines a longitudinal slot therein and into which the flange extends, whereby the flange and slot cooperate to define the extent of travel of the guard between a retracted position and an extended position.

5. The guarded surgical scalpel of claim 4 wherein one of the two sidewalls defines at least one L-shaped slot therein adjacent to a distal portion thereof and the blade carrier defines a first pin adjacent to a distal portion of the blade carrier, the first pin being removably located in the L-shaped slot.

6. The guarded surgical scalpel of claim 5 wherein one of the two sidewalls defines a cut-out adjacent to a proximal portion thereof and the blade carrier defines a second pin adjacent to a proximal portion thereof and removably located in the cut-out, wherein when the first pin is located in the L-shaped slot and the second pin is located in the cut-out, the blade carrier is fixed with respect to the handle.

7. The guarded surgical scalpel of claim 1 wherein said blade is removably connected to the blade carrier.

8. The guarded surgical scalpel of claim 7 wherein the blade includes a proximal tang defining a notch therein and the blade carrier defines a complementary notch for mating with the notch in the proximal tang of the blade.

9. A guarded surgical scalpel, comprising:
   an elongate handle;
   a guard;
   a first mounting means mounting the guard to the handle for allowing relative longitudinal movement between the guard and the handle;
   a blade carrier having a wedge movably mounted to the blade carrier, the wedge being movable to a position toward the blade carrier to facilitate removal of a blade from the blade carrier;
   a second mounting means mounting the blade carrier to the guard for allowing relative longitudinal movement between the blade carrier and the guard; and a third mounting means for mounting the blade carrier to the handle for rotary movement with respect to the handle.

10. The guarded surgical scalpel of claim 9 wherein the handle has an internal cavity and the blade carrier is removably mounted in the internal cavity of the handle and the guard is removably mounted in the internal cavity of the handle between the blade carrier and the handle.

11. The guarded surgical scalpel of claim 10 wherein said blade is removably connected to the blade carrier.

12. The guarded surgical scalpel of claim 11 wherein the blade includes a proximal tang defining a notch therein and the blade carrier defines a complementary notch for mating with the notch in the proximal tang of the blade.

13. The guarded surgical scalpel of claim 10 further comprising a means for removing a blade from the blade carrier.

* * * * *